US012502471B2

(12) United States Patent
Varasani

(10) Patent No.: US 12,502,471 B2
(45) Date of Patent: Dec. 23, 2025

(54) MONITORING RECIRCULATION

(71) Applicant: Bellco S.R.L., Mirandola (IT)

(72) Inventor: Michele Varasani, SantAgata (IT)

(73) Assignee: Bellco S.R.L., Mirandola (IT)

( * ) Notice: Subject to any disclaimer, the term of this patent is extended or adjusted under 35 U.S.C. 154(b) by 663 days.

(21) Appl. No.: 17/812,515

(22) Filed: Jul. 14, 2022

(65) Prior Publication Data

US 2023/0013525 A1 Jan. 19, 2023

Related U.S. Application Data

(60) Provisional application No. 63/221,737, filed on Jul. 14, 2021.

(51) Int. Cl.
*A61M 1/36* (2006.01)
*A61B 5/145* (2006.01)

(52) U.S. Cl.
CPC ........ *A61M 1/3658* (2014.02); *A61M 1/3661* (2014.02); *A61B 5/14535* (2013.01); *A61M 2205/18* (2013.01); *A61M 2205/3303* (2013.01); *A61M 2205/3334* (2013.01)

(58) Field of Classification Search
CPC .............. A61M 1/3658; A61M 1/3661; A61M 2205/18; A61M 2205/3303; A61M 2205/3334; A61M 1/1607; A61M 1/1609; A61B 5/14535; A61B 5/4836
See application file for complete search history.

(56) References Cited

U.S. PATENT DOCUMENTS

| | | | | |
|---|---|---|---|---|
| 6,409,700 B1 * | 6/2002 | Siegel, Jr. | A61M 1/3659 | 604/284 |
| 2002/0009385 A1 * | 1/2002 | Krivitski | A61M 1/3609 | 210/85 |
| 2006/0043007 A1 * | 3/2006 | Tarumi | A61M 1/3658 | 210/96.2 |
| 2010/0010427 A1 * | 1/2010 | Yu | A61M 1/1603 | 604/29 |
| 2021/0196879 A1 * | 7/2021 | Balter | A61B 5/14535 | |

FOREIGN PATENT DOCUMENTS

| | | | |
|---|---|---|---|
| EP | 2792377 A1 * | 10/2014 | A61M 1/16 |

* cited by examiner

*Primary Examiner* — Philip R Wiest
*Assistant Examiner* — Matthew Wrubleski

(57) ABSTRACT

An example medical system includes a hemodialysis device configured to receive blood from vasculature of a patient via an arterial line and to deliver blood to the vasculature of the patient via a venous line. The medical system includes a hematocrit sensor configured to generate a signal indicative of a hematocrit level of blood in at least one of the arterial line or the venous line. The medical system also includes processing circuitry configured to determine a change in blood volume of the patient over time based on the signal indicative of the hematocrit level, determine a threshold blood volume reduction over time for the patient, compare the change in the blood volume of the patient over time to the threshold blood volume reduction over time, and based on the comparison, generate an indication of vascular access recirculation.

13 Claims, 3 Drawing Sheets

MONITORING RECIRCULATION

This application claims the benefit of U.S. Provisional Application No. 63/221,737, filed Jul. 14, 2021, the entire contents of which are hereby incorporated by reference herein.

TECHNICAL FIELD

This disclosure relates to medical devices and hemodialysis.

BACKGROUND

Patients with renal disease may receive hemodialysis treatment, which may involve using a medical device, such as a dialyzer or an artificial kidney, to remove blood from the body of a patient, remove waste and extra fluid from the blood, balance electrolytes, and return the blood to the body of the patient.

SUMMARY

This disclosure describes a hemodialysis system configured to determine whether vascular access recirculation occurs during hemodialysis and, in some examples, generate a notification indicative of the vascular access recirculation. Vascular access recirculation occurs when some amount of blood intended to be placed back in a vein of a patient for circulation through the heart instead enters an arterial line to a dialysis device and dialyzed blood re-enters the dialysis device. In some examples, processing circuitry of the hemodialysis system is configured to determine a change in the blood volume of a patient over time based on a signal generated by a hematocrit sensor, compare the change in the blood volume over time to a threshold blood volume reduction over time, and determine whether there is vascular access recirculation based on the comparison. For example, the processing circuitry may generate an output indicative of vascular access recirculation in response to determining the difference in the change in the blood volume over time and the threshold blood volume reduction over time is greater than or equal to a predetermined difference threshold. In some examples, the processing circuitry may also be configured to determine an amount of vascular access recirculation.

Aspects of this disclosure are directed to techniques for determining an indication of an amount of vascular access recirculation. In some examples, a hemodialysis system includes a hemodialysis device configured to receive blood from vasculature of a patient via an arterial line and to deliver blood to the vasculature of the patient via a venous line; a hematocrit sensor configured to generate a signal indicative of a hematocrit level of blood in at least one of the arterial line or the venous line; and processing circuitry configured to: determine a change in blood volume of the patient over time based on the signal indicative of the hematocrit level; determine a threshold blood volume reduction over time for the patient; compare the change in the blood volume of the patient over time to the threshold blood volume reduction over time; and based on the comparison, generate an indication of vascular access recirculation.

In some examples, a method includes receiving, by a hemodialysis device, blood from a patient via an arterial line; delivering, by the hemodialysis device, blood to the patient via a venous line; generating, by the hemodialysis device, a signal indicative of a hematocrit level of blood in at least one of the arterial line or the venous line; determining, by the hemodialysis device, a change in blood volume of the patient over time based on the signal indicative of the hematocrit level; determining, by the hemodialysis device, a threshold blood volume reduction over time for the patient; comparing, by the hemodialysis device, the change in the blood volume of the patient over time to the threshold blood volume reduction over time; and based on the comparison, generating, by the hemodialysis device, an indication of vascular access recirculation.

In some examples, a non-transitory computer-readable storage medium includes instructions, that, when executed by processing circuitry, cause the processing circuitry to: determine a change in blood volume of a patient over time based on a signal indicative of a hematocrit level of blood from a patient in at least one of an arterial line or a venous line of a hemodialysis device; determine a threshold blood volume reduction over time for the patient; compare the change in the blood volume of the patient over time to the threshold blood volume reduction over time; and based on the comparison, generate an indication of vascular access recirculation.

The details of one or more examples are set forth in the accompanying drawings and the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
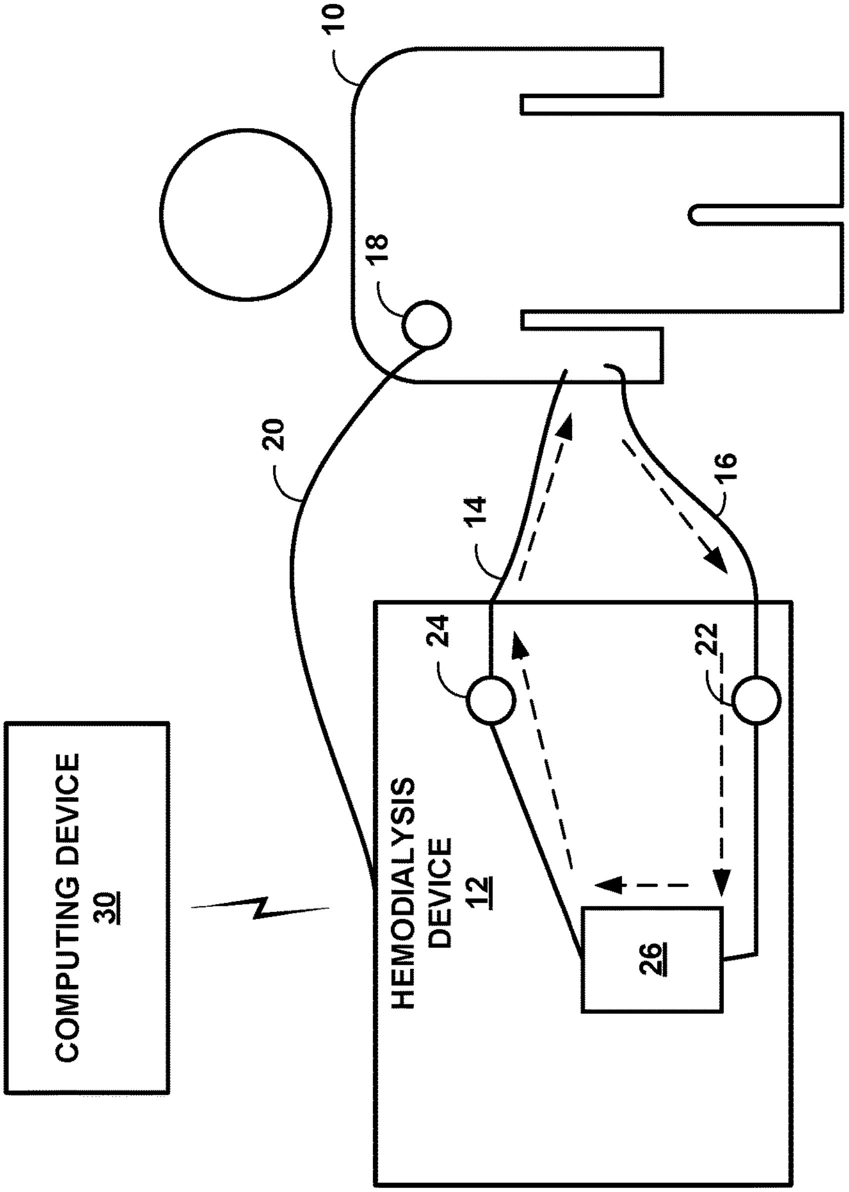
FIG. 1 is a conceptual diagram of an example hemodialysis system and a patient.

This disclosure describes a hemodialysis system, including a hemodialysis device, that is configured to determine whether vascular access recirculation occurs when the hemodialysis device is delivering hemodialysis treatment to a patient, as well as methods for determining vascular access recirculation is occurring or has occurred. Vascular access recirculation occurs when some amount of blood intended to be placed back in a vein of a patient for circulation through the heart instead enters an arterial line to a dialysis device and dialyzed blood re-enters the dialysis device. While some degree of vascular access recirculation may be expected in hemodialysis treatment, a higher degree of vascular access recirculation may be indicative of a relatively ineffective hemodialysis treatment session. For example, in some cases, levels of vascular access recirculation on the order of about 10% and above may be indicative that the hemodialysis treatment is less effective than desired. This is because dialyzed blood is being recirculated through the hemodialysis device without first circulating through the circulatory system of the patient. If known, such a condition may be addressable by a clinician, a patient, or a patient caretaker by taking one or more actions, such as by adjusting a position of a needle (relative to the patient) and/or by taking an action related to a catheter, the needle and/or catheter defining a pathway into vasculature of a patient. By addressing the condition, the clinician, the patient, or the patient caretaker may improve the efficacy of the hemodialysis treatment.

Vascular access recirculation can affect the efficacy of a hemodialysis session. The risk of vascular access recirculation and the amount of any vascular access recirculation may differ every hemodialysis session because vascular access recirculation depends on needle application or on the catheter status, both of which may be used to access the vasculature of patient. The patient being treated may not realize that there is vascular access recirculation, even if the amount of vascular access recirculation is relatively high. As such, the devices, systems, and methods described herein may provide more effective hemodialysis treatment for a patient by at least automatically monitoring for vascular access recirculation during a hemodialysis session and generating a timely notification in response to detecting vascular access recirculation. The notification may enable the user (e.g., clinician, the patient, or the patient caretaker) to take a responsive action to try to reduce the amount of vascular access recirculation and improve the efficacy of the hemodialysis, and, therefore possibly improve the therapeutic efficacy of the hemodialysis session.

Devices external to the hemodialysis device may be used to measure an amount of vascular access recirculation. However, such devices require set up time, measurement time, and the manual release of a bolus of fluid, such as saline, which may be undesirable and/or cumbersome for the patient (or patient caretaker) and/or a clinician. Additionally, because of the additional set up time and measurement time, such devices may not be regularly used for every hemodialysis treatment session for every patient. Moreover, such devices constitute additional equipment which a clinical facility or patient may need to purchase, maintain, and store. In contrast, the hemodialysis systems described herein utilize the same hemodialysis device that is delivering hemodialysis treatment to determine the existence of vascular access recirculation and/or the degree of vascular access recirculation that may occur during the delivery of hemodialysis treatment. This results in a more simple, easier to implement system to monitor vascular access recirculation.

One way of measuring an amount of vascular access recirculation may be to change the blood temperature of the blood being reintroduced into a patient and sense the temperature of the blood being input into the dialysis device via the arterial line. However, this technique may not provide a continuous monitor for the existence of vascular access recirculation and may not be very accurate because changing blood temperature of blood that is to be reintroduced into the patient may be very noticeable by, and even unpleasant to, the patient so any changes made to blood temperature should be relatively minor.

While receiving hemodialysis treatment, parameters of interest of the patient may be monitored via one or more sensors. For example, one or more hematocrit sensors may be located in the venous line that delivers blood to vasculature of the patient and/or the arterial line that delivers blood to a hemodialysis device and processing circuitry of a hemodialysis system may monitor signals from the hematocrit sensors as a way of monitoring for possible hypotensive episodes of a patient receiving the treatment. Blood volume of a patient is inversely proportional to the hematocrit levels in the blood and, therefore, blood volume (or relative changes in blood volume) can be determined based on the signal generated by a hematocrit sensor. A relatively fast drop in blood volume, as determined based on the signals generated by the one or more hematocrit sensors, may correlate to a hypotensive episode. Additionally, in some cases, one or more vital signs of a patient may be monitored via sensors, such as blood pressure, pulse, and temperature, to determine whether the hemodialysis treatment is being well-received by the patient.

While examples described herein also look for a change in blood volume over time (e.g., where the blood volume is determined based on the signals generated by one or more hematocrit sensors), the change in blood volume is over a longer period of time than the period of time that is used to detect a hypotensive episode. In addition, the change in blood volume over that is indicative of vascular access recirculation may be less than that required to characterize the change in blood volume as being indicative of a hypotensive episode.

FIG. 1 is a conceptual diagram of an example hemodialysis system and patient 10. The hemodialysis system includes a hemodialysis device 12 and computing device 30. The dashed arrows indicate the direction of blood flow during a hemodialysis session.

A clinician (or other user) may fluidically connect arterial line 16 to an inflow port (not shown) on hemodialysis device 12 and to an intravenous catheter (e.g., to a first lumen of the catheter), an arteriovenous fistula, or a synthetic graft (not shown) in patient 10 to provide access to the vasculature of patient 10. The arteriovenous fistula or the synthetic graft in the patient may be accessed, for example, via a needle or cannula. Arterial line 16 may be configured to facilitate the transport of blood from an artery of patient 10 to hemodialysis device 12. For example, blood from patient 10 may contain high levels of waste products due to kidney failure or kidney disease.

The clinician may also fluidically connect a venous line 14 to an outflow port (not shown) of the hemodialysis device 12 and to the intravenous catheter (e.g., to a second lumen of the catheter), the arteriovenous fistula or the synthetic graft in patient 10 to provide access to a vein of patient 10. Venous line 14 may be configured to return relatively cleaner blood from hemodialysis device 12 to the vasculature of patient 10.

Hemodialysis device 12 is configured to remove waste products from the blood received via arterial line 16. For example, hemodialysis device 12 may include a dialyzer 26 and/or one or more filters that may remove waste products and excess fluid from the blood received via arterial line 16. Dialyzer 26 may use a dialysate solution to remove the waste products and excess fluid from the blood of patient 10. Hemodialysis device 12 includes one or more sensors, such as arterial hematocrit sensor 22 and/or venous hematocrit sensor 24, and other sensors (not shown in FIG. 1), such as an arterial pressure sensor, a venous pressure sensor, an air sensor, an inflow pressure sensor (e.g., a sensor that senses the pressure of the inflow into dialyzer 26), a blood temperature sensor or the like. While depicted as part of hemodialysis device 12, in some examples, arterial hematocrit sensor 22 and/or venous hematocrit sensor 24 may be external to hemodialysis device 12, for example, in arterial line 16 or venous line 14.

In some examples, hemodialysis device 12 may be communicatively coupled to one or more external sensors, such as one or more sensors 18, via a link 20. Link 20 may be a wired link, a wireless link, an optical link, or any combination thereof. One or more sensors 18 may be configured to sense physiological parameters of interest of patient 10 and generate one or more signals indicative of the sensed one or more parameters of interest. For example, one or more sensors 18 may sense vitals of patient 10, such as blood pressure, temperature, oxygen content of the blood, etc.

Arterial hematocrit sensor 22 may be configured to sense a concentration of red blood cells in the blood of patient 10 that is entering hemodialysis device 12 prior to entering dialyzer 26. Venous hematocrit sensor 24 may be configured to sense a concentration of red blood cells in the blood of patient 10 that is exiting hemodialysis device 12 or exiting dialyzer 26. The concentration of red blood cells in the blood (as indicated by the hematocrit level) sensed by venous hematocrit sensor 24 should be expected to be higher than the concentration of red blood cells in the blood sensed by arterial hematocrit sensor 22, as dialyzer 26 removes excess fluid from the blood of patient 10, thereby reducing the blood volume while increasing the concentration of red blood cells in the blood of patient 10. In some examples, arterial hematocrit sensor 22 and venous hematocrit sensor 24 are optical sensors. In other examples, one or both hematocrit sensors 22, 24 can be other types of hematocrit sensors, such as, but not limited to, capacitive hematocrit sensors. Hemodialysis device 12 may also include a blood pump (not shown) which is configured to keep the blood of patient 10 flowing through hemodialysis device 12.

During a hemodialysis session, hemodialysis device 12 reduces the blood volume of patient 10. For example, in some cases, a patient with a normal BMI without hypotensive symptoms may experience a blood volume reduction of around 25% in a four hour hemodialysis treatment session. As such, there is an expected increase in the red blood cell concentration in the blood of patient 10 in venous line 14 compared to the blood of patient 10 in arterial line 16. Due to the expected inverse relationship between blood volume and hematocrit level, an indication of blood volume may therefore be sensed via hematocrit sensors, such as arterial hematocrit sensor 22 and venous hematocrit sensor 24. If hemodialysis device 12 is working properly and properly cleaning blood of patient 10, then a higher hematocrit level is observed for the blood in venous line 14 compared to the blood in arterial line 16. An increase in the sensed hematocrit level would therefore be indicative of the blood volume loss. More concentrated blood may be returned to patient 10 via venous line 14.

A hematocrit sensor (e.g., arterial hematocrit sensor 22 or venous hematocrit sensor 24) is configured to generate a signal indicative of a hematocrit level of blood in at least one of arterial line 16 or venous line 14. Sensing hematocrit in hemodialysis device 12 (as shown), in venous line 14, or in arterial line 16 may provide an indication of hematocrit level in venous line 14 and/or arterial line 16, as arterial hematocrit sensor 22 (as shown) is located prior to dialyzer 26 and venous hematocrit sensor 24 (as shown) is located after dialyzer 26 as blood flows through hemodialysis device 12. In some examples, the hematocrit sensor is venous hematocrit sensor 24.

Processing circuitry (FIG. 2) of hemodialysis device 12 and/or a separate computing device 30 is configured to determine a change in blood volume of patient 10 (e.g., the ultrafiltration volume) over time based on the signal generated by one or both hematocrit sensors 22, 24 and indicative of the hematocrit level. The processing circuitry may determine a threshold blood volume reduction over time for patient 10, such as by retrieving the threshold value from memory of hemodialysis device 12 or another device, such as computing device 30. The processing circuitry may compare the change in the blood volume of patient 10 over time to the threshold blood volume reduction over time and based on the comparison, generate an indication of vascular access recirculation. For example, during hemodialysis treatment of patient 10, in response to determining the difference between the change in the blood volume of patient 10 over time and the threshold blood volume reduction is greater than or equal to a predetermined difference threshold, the processing circuitry may cause a notification to be generated. The notification may indicate vascular access recirculation. The notification may be a visual notification, an audible notification, a tactile notification, or any combination thereof. By providing the notification, a clinician, patient 10, or a patient caregiver may become aware of the vascular access recirculation. Based on receiving the notification, clinician, patient 10, or the patient caregiver may cause the processing circuitry of the medical system to determine an amount of vascular access recirculation, adjust a needle position relative to patient 10, change a catheter defining at least part of the arterial and venous lines, pause dialysis treatment, or the like.

A difference between the determined change in the blood volume of patient 10 over time and the threshold blood volume reduction being greater than or equal to the predetermined difference threshold may indicate, for example, that a particular volume of blood is being reprocessed by hemodialysis device 12 due to vascular access recirculation. That is, because a particular volume of blood is being recirculated through hemodialysis device 12, the hematocrit level in the blood becomes may increase over time (as the blood becomes more concentrated). This increase in hematocrit level may be observed by the processing circuitry as a drop in blood volume due to the expected inverse relationship between blood volume and hematocrit level.

The predetermined difference threshold can be a change in blood volume that is may not be large enough to indicate a hypotensive episode, but may be indicative of recirculation. This could be monitored continuously during hemodialysis treatment or periodically. In some examples, the difference threshold is programmable by a clinician via a user interface of hemodialysis device 12 or via a computing device 30.

In some examples, computing device 30 may be a dedicated external programmer used to program hemodialysis device 12. In some examples, computing device 30 may be an off the shelf device, such as a smart phone, a tablet, a laptop computer, a desktop computer, or the like, and be configured to program hemodialysis device 12. Computing device 30 may include communication circuitry to communicatively connect to hemodialysis device 12 via a wireless, wired, or optical connection.

In some examples, hemodialysis device 12 (e.g., processing circuitry) determines a threshold blood volume reduction over time for patient 10. This threshold blood volume reduction over time may be based on a body size of patient 10. The body size may be a body weight, body mass index, and/or the like. There is a relationship between blood volume and body size, such that a larger body size may have a higher blood volume than a smaller body size. Therefore, one may expect a larger amount of blood volume reduction in a larger patient than in a smaller patient during a hemodialysis session. In some examples, hemodialysis device 12 determines the threshold blood volume reduction over time for patient 10 and stores the determined threshold in memory of hemodialysis device 12 or another device, such as computing device 30. In some examples, the threshold blood volume reduction is predetermined and stored in memory of hemodialysis device 12 or another device, and hemodialysis device 12 determines the threshold blood volume reduction by reading the value from the memory. In some examples, a clinician may enter the threshold blood volume reduction over time for patient 10 via a user interface or computing device 30.

Hemodialysis device 12 may monitor changes in blood volume of patient 10 over time during the dialysis session. For example, if there is a sudden drop in the blood volume of patient 10, that may be indicative of a hypotensive episode. Changes in the blood volume of patient 10 may also be indicative of vascular access recirculation. Different thresholds and different timelines may be involved in determining vascular access recirculation than in determining a hypotensive episode. Thus, the determination of vascular access recirculation is different than the determination of a hypotensive episode. For example, there may be vascular access recirculation when there is not a hypotensive episode and there may be a hypotensive episode when there is not vascular access recirculation. With a high level of vascular access recirculation, the hematocrit level in the hemodialysis device may quickly increase as some of the already processed blood is reprocessed without flowing through the body of patient 10, while the hematocrit in the body of patient 10 may not change or may only change by a relatively small amount.

In some examples, hemodialysis device 12 (e.g., processing circuitry) may determine an amount of vascular access recirculation (e.g., a quantitative or qualitative value indicative of the amount of vascular recirculation). In some examples, the determination of the amount of vascular access recirculation may be in response to generating the indication of vascular access recirculation. In some examples, the determination of the amount of vascular access recirculation may be in response to user input. For example, a clinician, patient 10, or a patient caregiver, may receive the indication of vascular access recirculation and may interact with hemodialysis device 12 through a user interface (FIG. 2) to initiate the determination of the amount of vascular access recirculation by hemodialysis device 12. In some examples, the user may initiate the determination of vascular access recirculation without receiving the indication of vascular access recirculation.

In some examples, to determine the amount of vascular access recirculation, hemodialysis device 12 may increase an ultrafiltration rate for a predetermined period of time. Patient 10 may not feel a temporary increase in the ultrafiltration rate. The predetermined period of time may be determined by hemodialysis device 12 prior to increasing the ultrafiltration rate. The ultrafiltration rate is a rate at which fluid is removed from the body of patient 10 during a hemodialysis session (such as 1 liter per hour). After the predetermined period of time, hemodialysis device 12 may determine a first hematocrit level based on a first signal indicative of a first hematocrit level in one of the arterial line or the venous line (e.g., a signal generated by arterial hematocrit sensor 22 or venous hematocrit sensor 24). After the predetermined period of time, hemodialysis device 12 may determine a second hematocrit level based on a second signal indicative of a second hematocrit level in another of the arterial line or the venous line (e.g., a signal generated by the other of arterial hematocrit sensor 22 or venous hematocrit sensor 24). Thus, hemodialysis device 12 may determine a hematocrit level using arterial hematocrit sensor 22 and determine another hematocrit level using venous hematocrit sensor 24. Hemodialysis device 12 may compare the first and second hematocrit levels and determine an amount of vascular access recirculation based on the comparison of the first and second hematocrit levels.

For example, if the hematocrit increases in the venous line by 5%, with no vascular access recirculation, then there should be no increase in the hematocrit in the arterial line. If there is complete 100% vascular access recirculation (e.g., all of the blood leaving hemodialysis device 12 is returned via arterial line 16 to hemodialysis device 12 and no intracorporeal blood enters arterial line 16), then the hematocrit in the arterial line should reflect the same increase as in the venous line (e.g., 5%). Hemodialysis device 12 may therefore determine the amount of vascular access recirculation by determining the difference between the hematocrit increase in the venous line and the hematocrit increase (if any) in the arterial line. For example, if the hematocrit increase in the venous line is 5% and the hematocrit increase in the arterial line is 1%, then the amount of vascular access recirculation would be on the order of 20% (e.g., the increase in hematocrit level in the arterial line divided by the increase in hematocrit level in the venous line).

In some examples, hemodialysis device 12 may generate a second notification in response to determining the amount of vascular access recirculation is greater than or equal to a threshold amount of vascular access recirculation. In some examples, the acceptable level of vascular access recirculation may be on the order of up to 5% to 20%, such as 10%. In some examples, the acceptable level of vascular access recirculation may be used as a threshold amount of vascular access recirculation. In some examples the threshold amount of vascular access recirculation may be programmable by a clinician, for example, through a user interface of hemodialysis device 12 or via computing device 30.

The second notification may be provided to a clinician or patient 10 via a user interface or through communication circuitry of hemodialysis device 12 to a computing device 30. The second notification may be a visual notification, a audible notification, a tactile notification, or any combination thereof. The second notification may include a notification to adjust a needle which may be attached to arterial line 16 or venous line 14, a notification to change a catheter that may be attached to arterial line 16 or venous line 14, a notification to pause dialysis treatment, an indication of the amount of vascular access recirculation, or the like.

For example, when a clinician requests hemodialysis device 12 to determine an amount of vascular access recirculation, or in response to the generation of the indication of vascular access recirculation, hemodialysis device 12 may determine the amount of vascular access recirculation. Hemodialysis device 12 may use the same hematocrit sensor signals which hemodialysis device 12 monitors to detect vascular access recirculation. To determine the amount of vascular access recirculation, hemodialysis device 12 may utilize information regarding extracorporeal blood volume (e.g., blood outside patient 10, such as the blood volume within arterial line 16, venous line 14, and hemodialysis device 12 (e.g., in the internal arterial line, the internal venous line, and dialyzer 26). For example, hemodialysis device 12 may determine an extracorporeal blood volume. In some examples, hemodialysis device 12 may read the extracorporeal blood volume from memory of hemodialysis device 12 or another device such as computing device 30. In some examples, hemodialysis device 12 may read information relating to the extracorporeal blood volume from memory and calculate the extracorporeal blood volume. For example, the memory of hemodialysis device 12 may separately store the blood volume of various components of the hemodialysis system, such as the hemodialysis device 12, dialyzer 26, arterial line 16, venous line 14, or the like. In some examples, a clinician may enter the extracorporeal blood volume via a user interface or a computing device 30 and hemodialysis device 12 may store the extracorporeal blood volume in memory.

Hemodialysis device 12 may also determine a blood flow rate through hemodialysis device 12. The blood flow rate may be the volume of blood processed by hemodialysis device 12 divided by the processing time. A clinician may prescribe a certain blood flow rate, such as 300 milliliters/minute or 500 milliliters/minute and program hemodialysis device 12 to operate at a given blood flow rate. Hemodialysis device 12 may determine a transit time for blood from when blood enters arterial line 16 to when blood exits the venous line 14. For example, hemodialysis device 12 may divide the extracorporeal blood volume by the blood flow rate. For example, if the extracorporeal blood volume is 500 milliliters and the blood flow is 500 milliliters/minute, then the transit time is 1 minute.

Based on the transit time, hemodialysis device 12 may determine the predetermined period of time referenced earlier in this disclosure, that is the predetermined period of time during which the ultrafiltration rate is to be increased. After the predetermined period of time, hemodialysis device 12 may determine the percentage of vascular access recirculation based on the comparison of the hematocrit levels sensed by venous hematocrit sensor 24 and arterial hematocrit sensor 22, as discussed above.

After the predetermined period of time, hemodialysis device 12 may return the ultrafiltration rate to the original programmed ultrafiltration rate. In some examples, hemodialysis device 12 may prevent or refrain from increasing the ultrafiltration rate a second time for at least another predetermined period of time. In some examples, hemodialysis device 12 may prevent or refrain from increasing the ultrafiltration rate more than a predetermined number of times during a hemodialysis session. Such measures may reduce a chance that the temporary increase(s) in ultrafiltration rate negatively impact patient 10, such as lead to a hypotension event.

Figure 2:
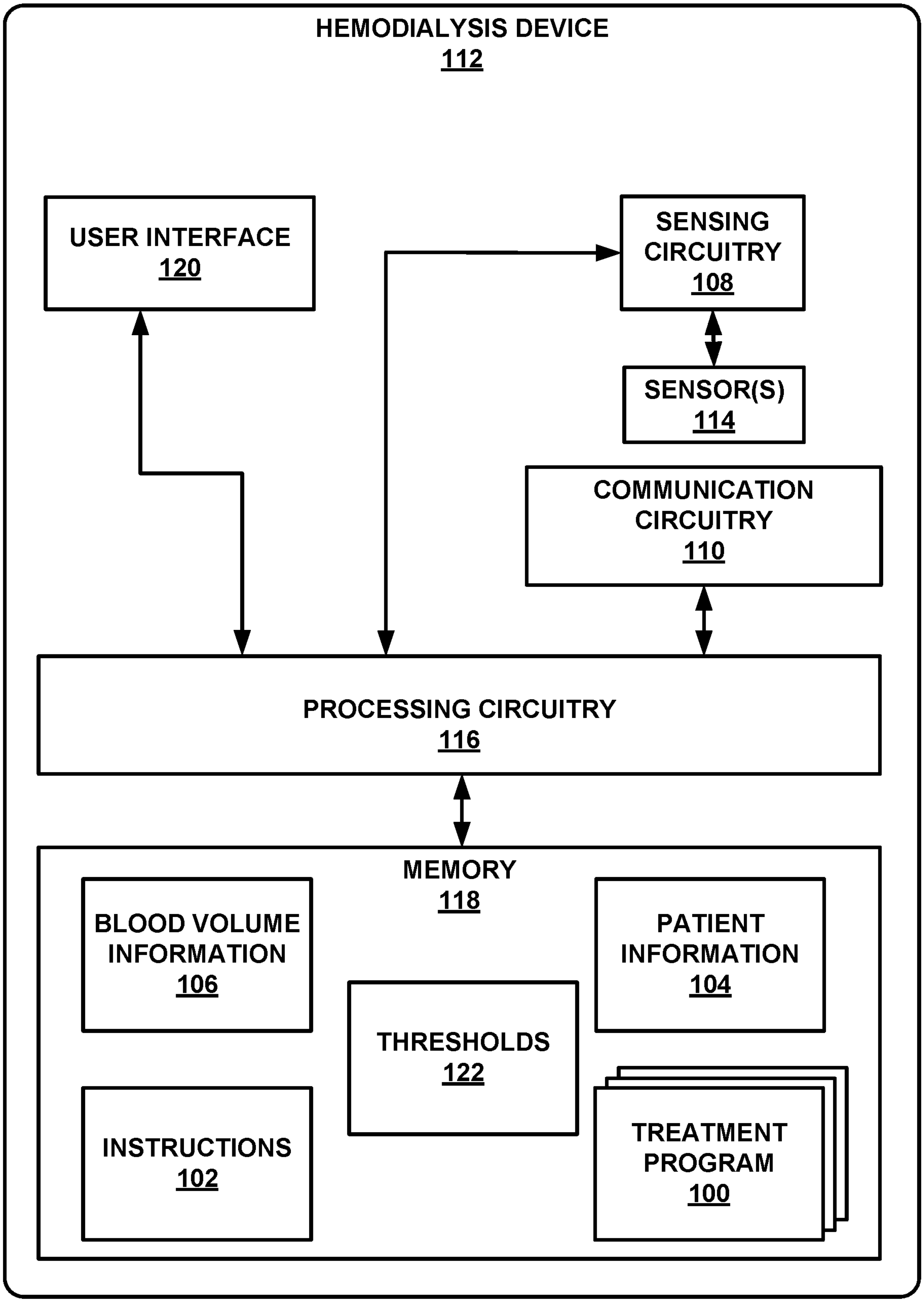
FIG. 2 is a functional block diagram illustrating an example hemodialysis device.

FIG. 2 is a functional block diagram illustrating an example hemodialysis device. In some examples, hemodialysis device 112 may be an example of hemodialysis device 12 of FIG. 1. While a number of components of the hemodialysis device 112 are shown, certain components are not shown. For example, in the case where hemodialysis device 112 may include a blood pump, one or more filters, and the other components which may be used to provide dialysis treatment to patient 10 (FIG. 1).

In the example of FIG. 2, hemodialysis device 112 includes processing circuitry 116, user interface 120, sensing circuitry 108, one or more sensors 114, communication circuitry 110, and memory 118. Processing circuitry 116 may include any of a microprocessor, integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 116 may include multiple components, such as any combination of one or more microprocessors, one or more DSPs, one or more ASICs, or one or more FPGAs, as well as other discrete or integrated logic circuitry, and/or analog circuitry.

Memory 118 may store instructions 102 which may include one or more program modules, which are executable by processing circuitry 116. When executed by processing circuitry 116, such instructions 102 may cause processing circuitry 116 to provide the functionality ascribed to them herein. Instructions 102 may be embodied in software and/or firmware. Memory 118 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Communication circuitry 110 may be configured to communicate with one or more sensors 18 or computing device 30 (both of FIG. 1) via wired, optical or wireless communication. In some examples, computing device 30 may communicate via near field communication (NFC) technologies (e.g., inductive coupling, NFC or other communication technologies operable at ranges less than 10-20 cm) and/or far field communication technologies (e.g., Radio Frequency (RF) telemetry according to the 802.11, Bluetooth® specification sets, or other communication technologies operable at ranges greater than NFC technologies. In some examples, a clinician may enter any of treatment program 100, patient information 104, blood volume information 106, or thresholds 122 on computing device 30 and communication circuitry 110 may receive the respective information from computing device 30, which processing circuitry 116 may store in memory 118.

In some examples, hemodialysis device 112 stores in memory 118 a treatment program 100 for patient 10. If hemodialysis device 112 is used to treat more than one patient, hemodialysis device 112 may store multiple treatment programs 100 such that each patient may have an associated personalized treatment program 100. Treatment program 100 may include various treatment parameters, such as ultrafiltration rate, that may be used when treating a patient, such as patient 10.

In some examples, a clinician or patient 10 (or patient caretaker) may interact with hemodialysis device 112 via user interface 120. User interface 120 may include a display, touch screen, keypad, mouse, microphone, speaker, or other device that may facilitate the interaction of a user, such as a clinician, and hemodialysis device 112. In some examples, user interface 120 may provide a first notification when processing circuitry 116 determines the occurrence of vascular access recirculation. For example, a user interface 120 may sound an alarm, or notify the clinician or patient 10 that there may be vascular access recirculation. In some examples, the first notification may be audible. In some examples, the first notification may be a visual notification that is displayed. In some examples, the first notification may be tactile. In some examples, processing circuitry 116 may send the first notification to another device via communication circuitry 110.

In some examples, user interface 120 may also provide a second notification when processing circuitry 116 determines that an amount of vascular access recirculation is greater than or equal to a threshold amount of vascular access recirculation (e.g., 10%). The second notification may, in some examples, include at least one of a notification to adjust a needle, a notification to change a catheter, a notification to pause dialysis treatment, or the amount of vascular access recirculation. For example, a display of user interface 120 may display a second notification that the amount of vascular access recirculation is 15% and may direct a clinician or patient 10 to adjust a needle. In some examples, processing circuitry 116 may send the second notification to another device via communication circuitry 110.

User interface 120 may also be used by a clinician to input treatment parameters for treatment program 100. User interface 120 may be used by a clinician to initiate a determination of the amount of vascular access recirculation. User interface 120 may also be used by a clinician to input thresholds 122. For example, thresholds 122 may store the threshold blood volume reduction over time, the difference threshold, and the threshold amount of vascular access recirculation. In some examples, any of thresholds 122 may be determined by hemodialysis device 112 and stored in thresholds 122.

Treatment program 100 may be separately programmable for each patient that may be treated using hemodialysis device 112. In this manner, a clinician may adapt treatment to an individual patient. In some examples, information regarding patient 10 may be stored in patient information 104. For example, a body size of patient 10 may be stored in patient information 104. In some examples, the body size of patient 10 may include a body weight or body mass index. In some examples, patient information 104 may include an estimated blood volume of patient 10.

In some examples, blood volume information 106 may be stored in memory 118. Blood volume information 106 may include an indication of the extracorporeal volume of blood during hemodialysis treatment. In some examples, blood volume information 106 may include an indication of the volume of blood within hemodialysis device 112. In some examples, blood volume information 106 may include an indication of the volume of blood which may be within arterial line 16 (FIG. 1) between patient 10 and hemodialysis device 112 and within venous line 14 (FIG. 1) between patient 10 and hemodialysis device 112.

Figure 3:
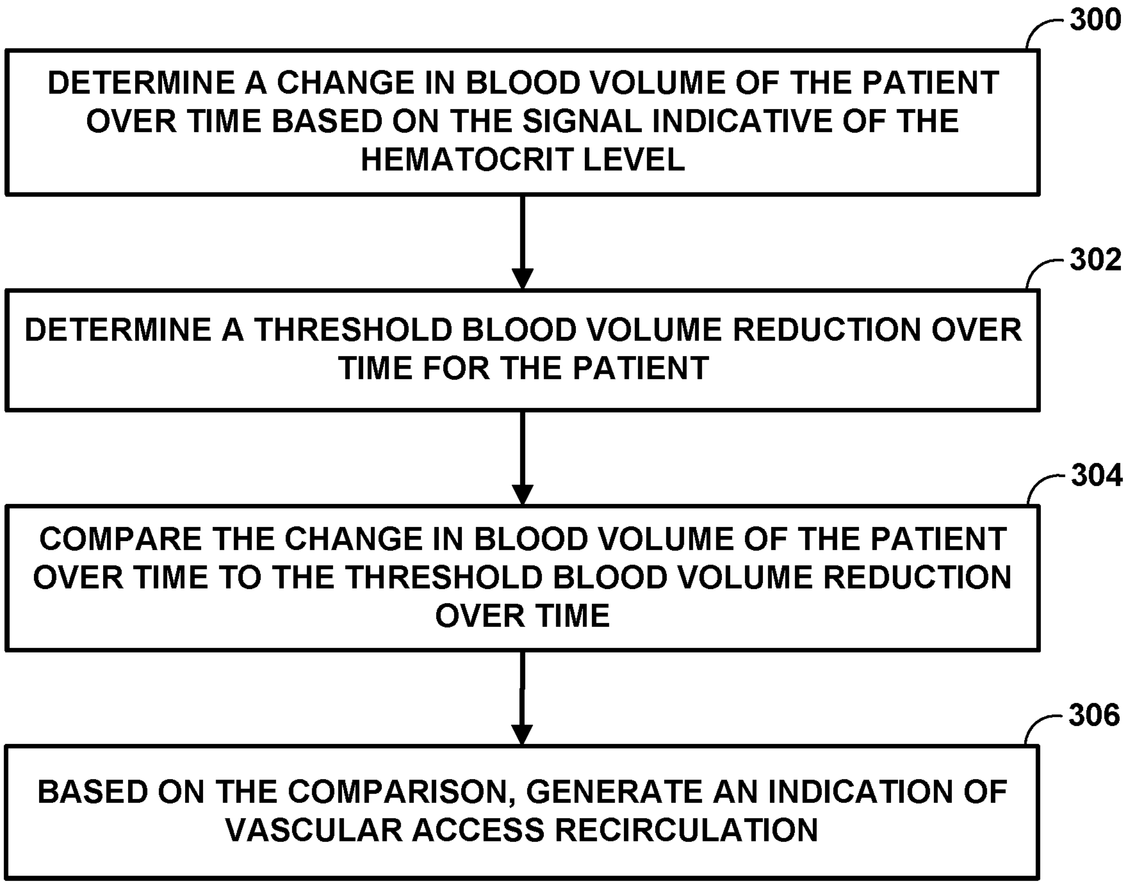
FIG. 3 is a flowchart illustrating an exemplary operation of a hemodialysis device in accordance with the techniques of this disclosure.

FIG. 3 is a flow diagram illustrating example techniques for changing treatment parameters of a medical device. While certain actions are described as being conducted by processing circuitry 116 of hemodialysis device 112, in some examples, any of these actions may be performed by processing circuitry of computing device 30 or by a combination of processing circuitry 116 and processing circuitry of computing device 30. Hemodialysis device 112 may receive blood from patient 10 via arterial line 16. For example, arterial line 16 may be coupled to an artery of patient 10 and blood may flow through arterial line 16 from patient 10 to an inflow port of hemodialysis device 112.

Hemodialysis device 112 may deliver treated (e.g., cleansed) blood to patient 10 via venous line 14. For example, venous line 14 may be coupled to a vein of patient 10 and blood may flow through venous line 14 from an outflow port of hemodialysis device 112 from hemodialysis device 112 to patient 10.

One or more sensors 114 of hemodialysis device 112 or a sensor coupled to hemodialysis device 112 may generate a signal indicative of a hematocrit level of blood in at least one of the arterial line or the venous line. For example, arterial hematocrit sensor 22 or venous hematocrit sensor 24 may sense a hematocrit level and generate a signal indicative of the hematocrit level. The signal from arterial hematocrit sensor 22 may be indicative of a hematocrit level in arterial line 16. The signal from venous hematocrit sensor 24 may be indicative of a hematocrit level in venous line 14.

Processing circuitry 116 may determine a change in blood volume of patient 10 over time based on the signal indicative of the hematocrit level (300). For example, the signal indicative of the hematocrit level may initially be indicative of an initial hematocrit level. After processing the blood of patient 10 over time, the signal indicative of the hematocrit level may change. Processing circuitry 116 may determine the change in blood volume of patient 10 over time based on the change in the signal indicative of the hematocrit level over that time.

Processing circuitry 116 may determine a threshold blood volume reduction over time for patient 10 (302). For example, processing circuitry 116 may determine the threshold blood volume reduction based on a body size of the patient or read the threshold blood volume reduction from thresholds 122 in memory 118.

Processing circuitry 116 may compare the change in the blood volume of the patient over time to the threshold blood volume reduction over time (304). For example, processing circuitry 116 may compare the change in the blood volume of the patient over time to a threshold blood volume reduction over time which may be stored in thresholds 122.

Based on the comparison, processing circuitry 116 may generate an indication of vascular access recirculation (306). For example, processing circuitry 116 may determine that the difference between the change in the blood volume of patient 10 over time and the threshold blood volume reduction over time is greater than or equal to a difference threshold that indicates that there is at least some level of vascular access recirculation occurring and generate the indication of vascular access recirculation in response to the determination. In some examples, the indication may include a notification indicative of vascular access recirculation.

In some examples, the signal indicative of the hematocrit level of blood in at least one of the arterial line or the venous line, is a first signal indicative of a first hematocrit level of blood, and processing circuitry 116 increases an ultrafiltration rate for a predetermined period of time. In some examples, one or more sensors 114 or a separate sensor generates a second signal indicative of a second hematocrit level of blood in another of the arterial line or the venous line. For example, the other of arterial hematocrit sensor 22 or venous hematocrit sensor 24 (both of FIG. 1) may generate the second signal. In some examples, after the predetermined period of time, processing circuitry 116 determines a first hematocrit level based on the first signal, and, after the predetermined period of time, determines the second hematocrit level based on the second signal. In some examples, processing circuitry 116 compares the first and second hematocrit levels. In some examples, processing circuitry 116 determines an amount of vascular access recirculation based on the comparison of the first and second hematocrit levels. For example, if the hematocrit increases in venous line 14 by 5%, with no vascular access recirculation, then there should be no increase in the hematocrit in arterial line 16. If there is complete 100% vascular access recirculation (e.g., all of the blood leaving hemodialysis device 12 is returned via arterial line 16 to hemodialysis device 12 and no intracorporeal blood enters arterial line 16), then the hematocrit in arterial line 16 should reflect the same increase as in venous line 14 (e.g., 5%). Processing circuitry 116 may therefore determine the amount of vascular access recirculation by determining the difference between the hematocrit increase in the venous line and the hematocrit increase (if any) in the arterial line. For example, if the hematocrit increase in the venous line is 5% and the hematocrit increase in the arterial line is 1%, then the amount of vascular access recirculation would be on the order of 20% (e.g., the increase in hematocrit level in the arterial line divided by the increase in hematocrit level in the venous line).

In some examples, processing circuitry 116 determines an extracorporeal blood volume and determines a blood flow rate through hemodialysis device 112. Based on the extracorporeal blood volume and the blood flow rate through the hemodialysis device, processing circuitry 116 may determine a transit time for blood from entering the arterial line to exiting the venous line and based on the transit time, determine the predetermined period of time.

In some examples, the notification is a first notification and processing circuitry 116 determines that the amount of vascular access recirculation is greater than or equal to a threshold amount of vascular access recirculation. Based on the determination that the amount of vascular access recirculation is greater than or equal to the threshold amount of vascular access recirculation, processing circuitry 116 may generate a second notification. In some examples, the second notification includes at least one of a notification to adjust a needle position relative to patient 10, a notification to change a catheter defining at least part of arterial line 16 and venous line 14, a notification to pause dialysis treatment, or the amount of vascular access recirculation. In some examples, the threshold amount of vascular access recirculation is 10 percent.

In some examples, the threshold blood volume reduction is based on a body size of the patient and an ultrafiltration volume setting for hemodialysis device 12. In some examples, the body size of the patient includes at least one of body weight or body mass index.

This disclosure includes the following non-limiting examples.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

Based upon the above discussion and illustrations, it is recognized that various modifications and changes may be made to the disclosed technology in a manner that does not necessarily require strict adherence to the examples and applications illustrated and described herein. Such modifications do not depart from the true spirit and scope of various aspects of the disclosure, including aspects set forth in the claims.

In at least one example, the functions described may be implemented in hardware, software, firmware, or any combination thereof. If implemented in software, the functions may be stored on or transmitted over as at least one instructions or code on a computer-readable medium and executed by a hardware-based processing unit. Computer readable media may include computer-readable storage media, which corresponds to a tangible medium such as data storage media, or communication media including any medium that facilitates transfer of a computer program from one place to another, e.g., according to a communication protocol. In this manner, computer readable media generally may correspond to (1) tangible computer-readable storage media which is non-transitory or (2) a communication medium such as a signal or carrier wave. Data storage media may be any available media that can be accessed by at least one computers or at least one processors to retrieve instructions, code and/or data structures for implementation of the techniques described in this disclosure. A computer program product may include a computer-readable medium.

By way of example, and not limitation, such computer-readable data storage media can include RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Combinations of the above should also be included within the scope of computer-readable media.

Instructions may be executed by at least one processors, such as at least one DSPs, general purpose microprocessors, ASICs, FPGAs, CPLDs, or other equivalent integrated or discrete logic circuitry. Accordingly, the term "processor," as used herein may refer to any of the foregoing structure or any other structure suitable for implementation of the techniques described herein. Also, the techniques could be fully implemented in at least one circuits or logic elements.

Any of the above-mentioned "processors," and/or devices incorporating any of the above-mentioned processors or processing circuitry, may, in some instances, be referred to herein as, for example, "computers," "computer devices," "computing device 30," "hardware computing device 30," "hardware processors," "processing units," "processing circuitry," etc. Computing device 30 of the above examples may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In some examples, the computing device 30*s* may be controlled by a proprietary operating system. Conventional operating systems control and schedule computer processes for execution, perform memory management, provide file system, networking, I/O services, and provide UI functionality, such as GUI functionality, among other things.

The techniques of this disclosure may be implemented in a wide variety of devices or apparatuses, including an integrated circuit (IC) or a set of ICs (e.g., a chip set). Various components, modules, or units are described in this disclosure to emphasize functional aspects of devices configured to perform the disclosed techniques, but do not necessarily require realization by different hardware units.

This disclosure includes the following non-limiting examples.

Example 1. A medical system comprising: a hemodialysis device configured to receive blood from vasculature of a patient via an arterial line and to deliver blood to the vasculature of the patient via a venous line; a hematocrit sensor configured to generate a signal indicative of a hematocrit level of blood in at least one of the arterial line or the venous line; and processing circuitry configured to: determine a change in blood volume of the patient over time based on the signal indicative of the hematocrit level; determine a threshold blood volume reduction over time for the patient; compare the change in the blood volume of the patient over time to the threshold blood volume reduction over time; and based on the comparison, generate an indication of vascular access recirculation.

Example 2. The medical system of example 1, wherein the indication comprises a notification indicative of vascular access recirculation.

Example 3. The medical system of example 2, wherein the hematocrit sensor comprises a first hematocrit sensor configured to generate a first signal indicative of a first hematocrit level in one of the arterial line or the venous line, the medical system further comprising a second hematocrit sensor configured to generate a second signal indicative of a second hematocrit level in another of the arterial line or the venous line, wherein the processing circuitry is configured to, in response to receiving a user input or generating the indication of vascular access recirculation: cause the hemodialysis device to increase an ultrafiltration rate for a predetermined period of time; after the predetermined period of time, determine the first hematocrit level based on the first signal; after the predetermined period of time, determine the second hematocrit level based on the second signal; compare the first and second hematocrit levels; and determine an amount of vascular access recirculation based on the comparison of the first and second hematocrit levels.

Example 4. The medical system of example 3, wherein the processing circuitry is further configured to: determine an extracorporeal blood volume; determine a blood flow rate through the hemodialysis device; based on the extracorporeal blood volume and the blood flow rate through the hemodialysis device, determine a transit time for blood from entering the arterial line to exiting the venous line; and based on the transit time, determine the predetermined period of time.

Example 5. The medical system of example 3 or example 4, wherein the notification comprises a first notification, and wherein the processing circuitry is further configured to: determine that the amount of vascular access recirculation is greater than or equal to a threshold amount of vascular access recirculation; and based on the determination that the amount of vascular access recirculation is greater than or equal to the threshold amount of vascular access recirculation, generate a second notification.

Example 6. The medical system of example 5, wherein the second notification comprises at least one of: a notification to adjust a needle position relative to the patient; a notification to change a catheter defining at least part of the arterial and venous lines; a notification to pause dialysis treatment; or the amount of vascular access recirculation.

Example 7. The medical system of example 5 or example 6, wherein the threshold amount of vascular access recirculation is 10 percent.

Example 8. The medical system of any of examples 1-7, wherein the threshold blood volume reduction is based on a body size of the patient and an ultrafiltration volume setting for the hemodialysis device.

Example 9. The medical system of example 8, wherein the body size of the patient comprises at least one of body weight or body mass index.

Example 10. A method comprising: receiving, by a hemodialysis device, blood from a patient via an arterial line; delivering, by the hemodialysis device, blood to the patient via a venous line; generating, by the hemodialysis device, a signal indicative of a hematocrit level of blood in at least one of the arterial line or the venous line; determining, by the hemodialysis device, a change in blood volume of the patient over time based on the signal indicative of the hematocrit level; determining, by the hemodialysis device, a threshold blood volume reduction over time for the patient; comparing, by the hemodialysis device, the change in the blood volume of the patient over time to the threshold blood volume reduction over time; and based on the comparison, generating, by the hemodialysis device, an indication of vascular access recirculation.

Example 11. The method of example 10, wherein the indication comprises a notification indicative of vascular access recirculation.

Example 12. The method of example 11, wherein the signal indicative of the hematocrit level of blood in at least one of the arterial line or the venous line, is a first signal indicative of a first hematocrit level of blood, and wherein the method further comprises: increasing, by the hemodialysis device, an ultrafiltration rate for a predetermined period of time; generating a second signal indicative of a second hematocrit level of blood in another of the arterial line or the venous line; after the predetermined period of time, determining a first hematocrit level based on the first signal; after the predetermined period of time, determining the second hematocrit level based on the second signal; comparing the first and second hematocrit levels; and determining an amount of vascular access recirculation based on the comparison of the first and second hematocrit levels.

Example 13. The method of example 12, further comprising: determining, by the hemodialysis device, an extracorporeal blood volume; determining, by the hemodialysis device, a blood flow rate through the hemodialysis device; based on the extracorporeal blood volume and the blood flow rate through the hemodialysis device, determining, by the hemodialysis device, a transit time for blood from entering the arterial line to exiting the venous line; and based on the transit time, determining, by the hemodialysis device, the predetermined period of time.

Example 14. The method of example 12 or example 13, the notification comprises a first notification, the method further comprising: determining, by the hemodialysis device, that the amount of vascular access recirculation is greater than or equal to a threshold amount of vascular access recirculation; and based on the determination that the amount of vascular access recirculation is greater than or equal to the threshold amount of vascular access recirculation, generating, by the hemodialysis device, a second notification.

Example 15. The method of example 14, wherein the second notification comprises at least one of: a notification to adjust a needle position relative to the patient; a notification to change a catheter defining at least part of the arterial and venous lines; a notification to pause dialysis treatment; or the amount of vascular access recirculation.

Example 16. The method of example 14 or example 15, wherein the threshold amount of vascular access recirculation is 10 percent.

Example 17. The method of any of examples 10-16, wherein the threshold blood volume reduction is based on a body size of the patient and an ultrafiltration volume setting for the hemodialysis device.

Example 18. The method of example 17, wherein the body size of the patient comprises at least one of body weight or body mass index.

Example 19. A non-transitory computer-readable storage medium comprising instructions, that, when executed by processing circuitry, cause the processing circuitry to: determine a change in blood volume of a patient over time based on a signal indicative of a hematocrit level of blood from a patient in at least one of an arterial line or a venous line of a hemodialysis device; determine a threshold blood volume reduction over time for the patient; compare the change in the blood volume of the patient over time to the threshold blood volume reduction over time; and based on the comparison, generate an indication of vascular access recirculation.

Example 20. The non-transitory computer-readable storage medium of example 19, wherein the signal indicative of the hematocrit level of blood in at least one of the arterial line or the venous line, is a first signal indicative of a first hematocrit level of blood, wherein the instructions further cause the processing circuitry to: cause the hemodialysis device to increase an ultrafiltration rate for a predetermined period of time; after the predetermined period of time, determine the first hematocrit level based on the first signal; after the predetermined period of time, determine a second hematocrit level based on a second signal indicative of a second hematocrit level of blood in another of the arterial line or the venous line; compare the first and second hematocrit levels; and determine an amount of vascular access recirculation based on the comparison of the first and second hematocrit levels.

Various examples have been described. These and other examples are within the scope of the following claims.

What is claimed is:

1. A medical system comprising:
- a hemodialysis device configured to receive blood from vasculature of a patient via an arterial line and to deliver blood to the vasculature of the patient via a venous line;
- a first hematocrit sensor configured to generate a first signal indicative of a first hematocrit level of blood in one of the arterial line or the venous line;
- a second hematocrit sensor configured to generate a second signal indicative of a second hematocrit level in another of the arterial line or the venous line; and
- processing circuitry configured to:
  - determine a change in blood volume of the patient over time based on the first signal indicative of the first hematocrit level;
  - determine a threshold blood volume reduction over time for the patient;
  - compare the change in the blood volume of the patient over time to the threshold blood volume reduction over time; and
  - based on the comparison, generate an indication of vascular access recirculation, wherein the indication comprises a notification for output, the notification indicative of vascular access recirculation;
- wherein the processing circuitry is configured to, in response to receiving a user input or generating the indication of vascular access recirculation:
  - determine an extracorporeal blood volume;
  - determine a blood flow rate through the hemodialysis device;
  - based on the extracorporeal blood volume and the blood flow rate through the hemodialysis device, determine a transit time for blood from entering the arterial line to exiting the venous line;
  - based on the transit time, determine a first period of time;
  - cause the hemodialysis device to temporarily increase an ultrafiltration rate for the first period of time;
  - after the first period of time, determine the first hematocrit level based on the first signal;
  - after the first period of time, determine the second hematocrit level based on the second signal;
  - compare the first and second hematocrit levels; and
  - determine an amount of vascular access recirculation based on the comparison of the first and second hematocrit levels.

2. The medical system of claim 1, wherein the notification comprises a first notification, and wherein the processing circuitry is further configured to:
- determine that the amount of vascular access recirculation is greater than or equal to a threshold amount of vascular access recirculation; and
- based on the determination that the amount of vascular access recirculation is greater than or equal to the threshold amount of vascular access recirculation, generate a second notification for output, the second notification indicating that the amount of vascular access recirculation is greater than or equal to the threshold amount of vascular access recirculation.

3. The medical system of claim 2, wherein the second notification further comprises at least one of:
- a notification to adjust a needle position relative to the patient;
- a notification to change a catheter defining at least part of the arterial and venous lines;
- a notification to pause dialysis treatment; or
- the amount of vascular access recirculation.

4. The medical system of claim 2, wherein the threshold amount of vascular access recirculation is 10 percent.

5. The medical system of claim 1, wherein the threshold blood volume reduction is based on a body size of the patient and an ultrafiltration volume setting for the hemodialysis device.

6. The medical system of claim 5, wherein the body size of the patient comprises at least one of body weight or body mass index.

7. A method comprising:
- receiving, by a hemodialysis device, blood from a patient via an arterial line;
- delivering, by the hemodialysis device, blood to the patient via a venous line;
- generating, by the hemodialysis device, a first signal indicative of a first hematocrit level of blood in one of the arterial line or the venous line;
- generating, by the hemodialysis device, a second signal indicative of a second hematocrit level of blood in another of the arterial line or the venous line;
- determining, by the hemodialysis device, a change in blood volume of the patient over time based on the first signal indicative of the first hematocrit level;
- determining, by the hemodialysis device, a threshold blood volume reduction over time for the patient;
- comparing, by the hemodialysis device, the change in the blood volume of the patient over time to the threshold blood volume reduction over time; and
- based on the comparison, generating, by the hemodialysis device, an indication of vascular access recirculation, wherein the indication comprises a notification for output, the notification indicative of vascular access recirculation; and
- in response to receiving a user input or generating the indication of vascular access recirculation:
  - determining, by the hemodialysis device, an extracorporeal blood volume;
  - determining, by the hemodialysis device, a blood flow rate through the hemodialysis device;
  - based on the extracorporeal blood volume and the blood flow rate through the hemodialysis device, determining, by the hemodialysis device, a transit time for blood from entering the arterial line to exiting the venous line; and based on the transit time, determining, by the hemodialysis device, a first period of time;

temporarily increasing, by the hemodialysis device, an ultrafiltration rate for the first period of time;

after the first period of time, determining a first hematocrit level based on the first signal;

after the first period of time, determining the second hematocrit level based on the second signal;

comparing the first and second hematocrit levels; and determining an amount of vascular access recirculation based on the comparison of the first and second hematocrit levels.

8. The method of claim 7, the notification comprises a first notification, the method further comprising:

determining, by the hemodialysis device, that the amount of vascular access recirculation is greater than or equal to a threshold amount of vascular access recirculation; and based on the determination that the amount of vascular access recirculation is greater than or equal to the threshold amount of vascular access recirculation, generating, by the hemodialysis device, a second notification for output, the second notification indicating that the amount of vascular access recirculation is greater than or equal to the threshold amount of vascular access recirculation.

9. The method of claim 8, wherein the second notification further comprises at least one of:

a notification to adjust a needle position relative to the patient;

a notification to change a catheter defining at least part of the arterial and venous lines;

a notification to pause dialysis treatment; or the amount of vascular access recirculation.

10. The method of claim 8, wherein the threshold amount of vascular access recirculation is 10 percent.

11. The method of claim 7, wherein the threshold blood volume reduction is based on a body size of the patient and an ultrafiltration volume setting for the hemodialysis device.

12. The method of claim 11, wherein the body size of the patient comprises at least one of body weight or body mass index.

13. Non-transitory computer-readable storage media comprising instructions, that, when executed by processing circuitry, cause the processing circuitry to:

determine a change in blood volume of a patient over time based on a first signal indicative of a first hematocrit level of blood from a patient in one of an arterial line or a venous line of a hemodialysis device;

determine a threshold blood volume reduction over time for the patient;

compare the change in the blood volume of the patient over time to the threshold blood volume reduction over time; and based on the comparison, generate an indication of vascular access recirculation, wherein the indication comprises a notification for output, the notification indicative of vascular access recirculation, and wherein the instructions cause the processing circuitry to, in response to receiving a user input or generating the indication of vascular access recirculation:

determine an extracorporeal blood volume;

determine a blood flow rate through the hemodialysis device;

based on the extracorporeal blood volume and the blood flow rate through the hemodialysis device, determine a transit time for blood from entering the arterial line to exiting the venous line;

based on the transit time, determine a first period of time;

cause the hemodialysis device to temporarily increase an ultrafiltration rate for the first period of time;

after the first period of time, determine the first hematocrit level based on the first signal;

after the first period of time, determine a second hematocrit level based on a second signal indicative of a second hematocrit level in another of the arterial line or the venous line;

compare the first and second hematocrit levels; and determine an amount of vascular access recirculation based on the comparison of the first and second hematocrit levels.

* * * * *